United States Patent
Cipolletti et al.

(10) Patent No.: US 11,505,518 B2
(45) Date of Patent: Nov. 22, 2022

(54) METHOD FOR THE PRODUCTION OF CANNABINOIDS FROM TYPES OF INDUSTRIAL HEMP

(71) Applicant: INALCO S.R.L., Milan (IT)

(72) Inventors: Giovanni Cipolletti, Milan (IT); Luana Vagnoli, Quarata-Arezzo (IT); Marina Matulli, Granaglione (IT); Barbara Febbruari, Serravalle Pistoiese (IT); Jacopo Chini, Florence (IT)

(73) Assignee: INALCO S.R.L., Milan (IT)

( * ) Notice: Subject to any disclaimer, the term of this patent is extended or adjusted under 35 U.S.C. 154(b) by 0 days.

(21) Appl. No.: 16/634,311

(22) PCT Filed: Jul. 26, 2018

(86) PCT No.: PCT/EP2018/070275
§ 371 (c)(1),
(2) Date: Jan. 27, 2020

(87) PCT Pub. No.: WO2019/020738
PCT Pub. Date: Jan. 31, 2019

(65) Prior Publication Data
US 2020/0181050 A1 Jun. 11, 2020

(30) Foreign Application Priority Data
Jul. 26, 2017 (IT) .......... 102017000085508

(51) Int. Cl.
| | | |
|---|---|---|
| C07C 37/00 | (2006.01) | |
| C07C 37/84 | (2006.01) | |
| C07C 37/50 | (2006.01) | |
| B01D 11/02 | (2006.01) | |
| B01D 11/04 | (2006.01) | |

(52) U.S. Cl.
CPC ........ *C07C 37/004* (2013.01); *B01D 11/0288* (2013.01); *B01D 11/04* (2013.01); *B01D 11/0492* (2013.01); *C07C 37/50* (2013.01); *C07C 37/84* (2013.01); *C07C 2601/16* (2017.05)

(58) Field of Classification Search
None
See application file for complete search history.

(56) References Cited

U.S. PATENT DOCUMENTS

| | | |
|---|---|---|
| 2006/0167283 A1 | 7/2006 | Flockhart et al. |
| 2015/0038567 A1 | 2/2015 | Herkenroth et al. |
| 2015/0203434 A1 | 7/2015 | Flockhart et al. |
| 2016/0214920 A1 | 7/2016 | Nadal |
| 2017/0022132 A1 | 1/2017 | Mona, III et al. |
| 2019/0010106 A1* | 1/2019 | Oroskar ............... C07C 51/47 |

FOREIGN PATENT DOCUMENTS

| | | |
|---|---|---|
| WO | 20160153347 A1 | 9/2016 |
| WO | 20160187679 A1 | 12/2016 |

OTHER PUBLICATIONS

International Search Report and Written Opinion for PCT/EP2018/070275, dated Sep. 26, 2018.

* cited by examiner

*Primary Examiner* — Rosalynd A Keys
(74) *Attorney, Agent, or Firm* — Troutman Pepper Hamilton Sanders LLP (Rochester)

(57) ABSTRACT

The present invention describes a process for the production of (−)-cannabidiol (CBD) from industrial hemp by means of an extraction followed by two alternative working processes: a process A which provides extraction with solvents first to an alkaline pH and then to acidic pH to isolate the carboxyl form of the CBD which is then subjected to decarboxylation and a process B which provides the elimination of waxes and pitches and then purification by chromatography. At the end of both alternative working processes the CBD is crystallized obtained in high purity crystalline form.

34 Claims, 1 Drawing Sheet

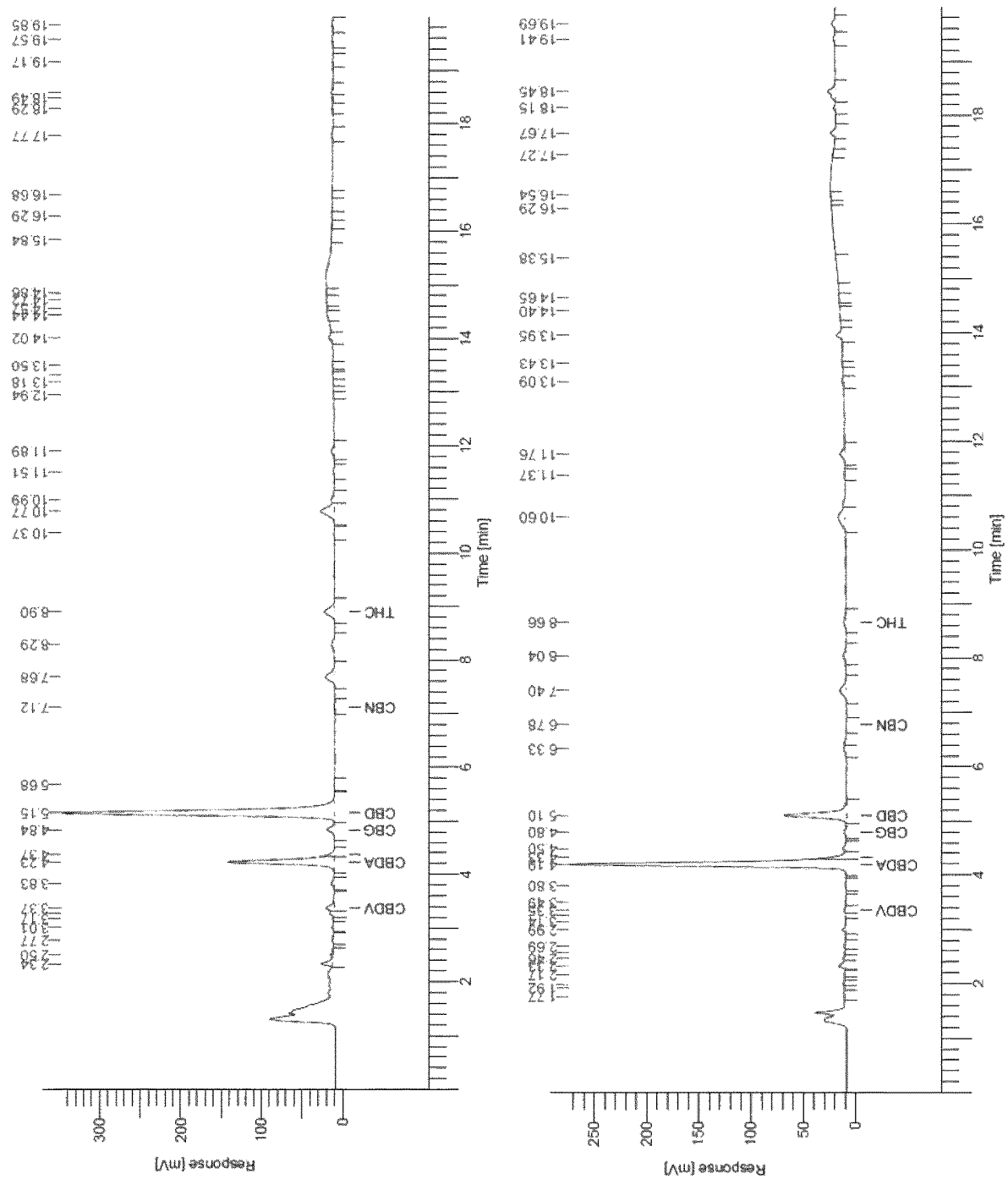

METHOD FOR THE PRODUCTION OF CANNABINOIDS FROM TYPES OF INDUSTRIAL HEMP

This application is a national stage application under 35 U.S.C. § 371 of PCT Application No. PCT/EP2018/070275, filed Jul. 26, 2018, which claims the priority benefit of Italian Patent Application No. 102017000085508, filed Jul. 26, 2017.

FIELD OF THE INVENTION

The present invention relates to the field of the extraction of cannabinoids from a vegetal matrix; particularly, it refers to the extraction of (−)-cannabidiol (CBD) and obtaining in the form of high purity crystal from hemp types.

BACKGROUND

Cannabinoids or cannabinols are chemicals of natural origin and biochemically classified as terpenophenols. They are compounds united by the ability to interact with cannabinoid receptors.

With the term cannabinoids it is generally identified a family of chemical compounds present in Cannabis sativa.

To date, about seventy of such compounds have been identified, among which the most important are:

tetrahydrocannabinol (THC, Δ9-THC), cannabidiol (CBD), tetrahydrocannabivarin (THCV), cannabinol (CBN), cannabichromene (CBC), cannabicyclol (CBL), cannabielsoin (CBE), cannabigerol (CBG), cannabinodiol (CBND), cannabitriol (CBT), cannabivarin (CBV), cannabidivarin (CBDV), cannabichromevarin (CBCV), cannabigerovarin (CBGV), and cannabigerol monoethyl ether (CBGM).

Recently Sativex, a drug extracted from Cannabis sativa, with a standardized cannabinoid content (THC and CBD), has been placed on the market.

Cannabinoids are found in the Cannabis sativa hemp plant in the form of their carboxyl derivatives, the cannabinoid carboxylic acids, from which the so-called "neutral cannabinoids" are derived by decarboxylation, i.e. the $CO_2$ elimination. Thus, for example, cannabidiol (CBD) is formed by the cannabidiolic acid (CBDA) decarboxylation.

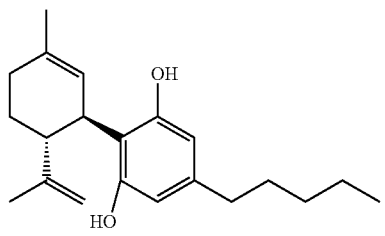

(−)-CBD
2-((1R,6R)-3-methyl-6-(prop-1-en-2-yl)cyclohex-2-enyl)-5-pentylbenzene-1,3-diol

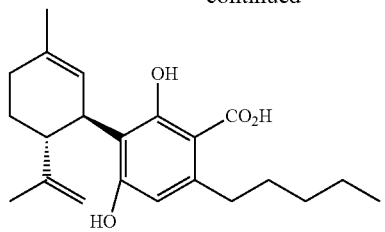

Cannabidiolic Acid (CBDA)
2,4-dihydroxy-3-((1R,6R)-3-methyl-6-(prop-1-en-2-yl)-cyclohex-2-enyl)-6-pentylbenzoic acid The (−)-cannabidiol (CBD) can be found in the plant both in its acidic form (CBDA) and in the decarboxylated one (CBD). The greater or lesser presence of one or the other form of the cannabinoid inside the biomass can depend both on the plant growing conditions and therefore on environmental parameters, and on the conditions used for the subsequent processing and storage phases. In the treatment processes of industrial hemp, the biomass can in fact undergo to a drying phase that can lead, due to heating, to the decarboxylation of the acid form of the cannabinoid (CBDA) in its decarboxylated form (CBD). This decarboxylation process can take place even at low temperature (R.T.) if the biomass is stored for long times before its use.

The isolation processes of neutral cannabinoids, particularly CBD, known at the state of the art (see for example what described in US2015/0038567) turn out to be rather laborious and it is not always possible to obtain them with high purity with processes that can be easily used on industrial scale.

The object of the present invention is to provide a process for producing from industrial hemp types of CBD, or other neutral cannabinoids, in high purity crystalline form.

SUMMARY OF THE INVENTION

The present invention solves the aforementioned problems by a process for the CBD production or other neutral cannabinoid, said process comprising:

i) contacting biomass containing the CBD and/or CBDA, or said other neutral cannabinoid or in the form of carboxylic acid, with an extraction solvent for at least 10 minutes at a temperature from 0° C. to the solvent reflux temperature, to obtain, after biomass removal, an extraction solution; said extraction solvent selected from the group consisting of pentane, hexane, heptane, octane, methylcyclohexane, acetone, propanol, ethanol, methanol, ethyl acetate, toluene, methylene chloride and mixtures thereof;

continuing according to a process (A) comprising:

ii-a) contacting the extraction solution with a hydro-alcoholic solution and adjust the pH to 7.5-12.5 with a suitable alkaline solution, to obtain, after phases separation, a first hydro-alcoholic phase and a first organic phase; in the case of the extraction solvent is a water-miscible solvent add also a first water-immiscible solvent selected from the group consisting of pentane, hexane, heptane, methylcyclohexane and mixtures thereof;

iii-a) contacting the first hydro-alcoholic phase with a second water-immiscible solvent and an acid solution suitable to bring the pH to 2.0-6.5 to obtain a second organic phase and a second hydro-alcoholic phase; said second water-immiscible solvent selected from the group consisting of pentane, hexane, heptane, methylcyclohexane and mixtures thereof;

iv-a) concentrating the second organic phase and subjecting the resulting oil to heating at a temperature between 65° C. and 180° C. for a time of at least 10 minutes to obtain the decarboxylation of the CBDA to CBD;

or continuing according to a process (B) comprising:

ii-b) concentrating the extraction solution until obtaining an extraction oil and contacting the extraction oil with an alcohol at a temperature less than 20° C. for at least 10 minutes to obtain a suspension of extract and waxes, said alcohol selected from the group consisting of methanol, ethanol, propanol, and mixtures thereof;

iii-b) filtering and concentrating the suspension to obtain a wax-free extraction oil and contacting the wax-free extraction oil with a water-immiscible organic solvent and a hydro-alcoholic solution to obtain an organic phase containing the wax- and pitch-free extract and a hydro-alcoholic phase containing pitches;

iv-b) concentrating the organic phase containing the wax- and pitch-free extract and subjecting to silica gel chromatography using a suitable eluent phase and collecting the fractions containing CBD, or said other neutral cannabinoid;

and concluding with v) CBD, or said other neutral cannabinoid, crystallization from a third water-immiscible solvent selected from the group consisting of pentane, hexane, heptane, octane, methylcyclohexane and mixtures thereof.

Surprisingly it has been seen that the (−)-cannabidiol (CBD) extraction and isolation method described in the present invention can be applied to "biomasses" having any ratio of the acidic form (CBDA) and the decarboxylated one (CBD) through any one of the two processes defined herein as: Process A and Process B.

It is to be noted that, due to its specific simplicity, the process A is indicated for processing in the pharmaceutical field which are subject to more restrictive rules.

In addition to the recovery of CBD, the process B also applies to obtaining other cannabinoids (e.g. CBG, CBN, etc.).

DETAILED SPECIFICATION OF THE INVENTION

According to the invention the pentane, hexane, heptane and octane solvents are intended as n-pentane, n-hexane, n-heptane, n-octane or isomers mixtures thereof. Preferably according to the present invention, the raw material (i.e. the biomass) used is industrial hemp (species *Cannabis sativa*; subspecies *Sativa*). As an alternative, and equally preferably, types of industrial hemp may be used, for example: Antal, Armanca, Beniko, Bialobrzeskie, Cannakomp, Carma, Carmagnola, Carmaleonte, Chamaeleon, Codimoro, CS, Dacia Sacuieni, Delta-Ilosa, Delta-405, Denise, Diana, Dioica 88, Eletta Campana, Epsilon 68, Fedora 17, Felina 32, Férimon, Fibranova, Fibrol, Finola, Futura 75, Ivory, KC Bonusz, KC Dora, KC Virtus, KC Zuzuna, Kompolti, KompoltiHibrid TC, Lipko, Lovrin 110, Marcello, Markant, Monica, Rajan, Ratza, Santhica 23, Santhica 27, Santhica 70, SecuieniJubileu, Silvana, Szarvasi, Tiborszallasi, Tisza, Tygra, Uniko B, Uso-31, Wielkopolkie, Wojko, Zenit.

The biomass is preferably micronized before being subjected to solvent extraction according to the process of the present invention.

Process A:

Preferably the CBDA and CBD extraction takes place by keeping the hemp in contact with a solvent conveniently chosen from the group consisting of pentane, hexane, heptane, octane, methylcyclohexane and mixtures thereof; more preferably hexane (n-hexane or isomers mixture) as extraction solvent is used.

The extraction according to process A preferably takes place at a temperature between 0° C. and 35° C., more preferably between 10 and 25° C., for a time of at least 10 minutes.

According to process A of the present invention the acid form (CBDA) is separated from the decarboxylated form (CBD) and from the impurities by the addition of a hydro-alcoholic solution in which the alcohol is conveniently selected from the group consisting of ethanol, methanol, preferably methanol. The separation takes place by adding, under stirring, of a suitable alkaline solution, preferably a 30% NaOH solution is used, bringing the pH between 7.5 and 12.5, more preferably between 8.0 and 8.5, even more preferably between 8.2 and 8.3. It has been observed that pH 8.2-8.3 is particularly advantageous in order not to allow to extract in the hydroalcoholic phase also fatty acids such as omega-3 or omega-6 sometimes present, even in substantial amounts in the starting biomass.

The first hydro-alcoholic phase is recovered and the CBDA is extracted by the addition, under stirring, of a second more or less apolar water-immiscible solvent, preferably hexane (n-hexane or isomers mixture) is used, and of an acid solution, preferably an acetic acid solution is used, bringing the pH between 6.5 and 2.0, preferably 4.5 and 5.5, even more preferably between 4.8 and 5.2.

The second organic phase is concentrated to oil and the CBDA in it contained is decarboxylated to CBD keeping the oil at a temperature between 65° C. and 180° C. for a time of at least 10 minutes.

The CBD is then crystallized.

Process B

The CBDA and CBD extraction takes place by keeping the hemp in contact with a solvent preferably selected from the group consisting of acetone, propanol, ethanol, methanol, ethyl acetate, toluene, n-hexane or hexane-mixture of isomers; more preferably methanol, at the reflux temperature of the solvent for a time of at least 10 minutes. If necessary, the suspension is kept under stirring until complete decarboxylation of the CBDA to CBD.

The suspension can be maintained at reflux for even 60 hours or more.

The biomass is separated by filtration or centrifugation and the solution containing the CBD is concentrated up to oil.

The waxes present in the extraction solution are eliminated by the addition of an alcohol, preferably methanol is used, maintaining the temperature below 20° C., preferably 4-10° C., even more preferably 4° C., for a time of at least 10 minutes. The suspension is filtered and the wax-free solution is concentrated to oil.

The pitches are removed from the oil by adding, under stirring, of a suitably selected solvent in the group consisting of toluene, pentane, hexane, heptane, octane and mixtures thereof; preferably hexane (n-hexane or mixture of isomers) is used; and a hydroalcoholic solution in which the alcohol is suitably selected from group consisting of ethanol and methanol; preferably methanol is used.

The hexane phase is concentrated to oil and loaded onto a silica gel column using as an eluting phase preferably a mixture of hexane (n-hexane or mixture of isomers) and ethyl acetate preferably in a ratio between 20:1 and 5:1, even more preferably 10:1.

The fractions containing the purified CBD are pooled together and concentrated in oil and the CBD contained in it is crystallized.

Crystallization

The crystallization of the CBD, whether it comes from the process A or from the process B, occurs by adding, under stirring, 0.3-3 volumes, preferably 0.5-1, even more preferably 0.6 volumes of solvent compared to the oil weight. The solvent is conveniently selected from the group consisting of pentane, hexane, heptane, octane and methylcyclohexane, preferably hexane or heptane (or mixtures of their isomers) or methylcyclohexane at a temperature of less than 30° C. for a time of at least 10 minutes, is used as the crystallization solvent. Crystallization is optionally triggered by the addition of a minimum amount of crystal CBD.

This crystallization step can optionally be repeated a second time to obtain a product with an even higher purity by adding, under stirring, 0.3-3 volumes, preferably 0.5-2.5, still more preferably 2 volumes of solvent with respect to the oil weight.

An advantageous aspect of the present invention is that processes A and B can be integrated because process steps from ii-b to iv-b can be applied to the first organic phase obtained from step ii-a of process A to recover the CBD, or other neutral cannabinoid, in it contained.

The present invention might be better understood in the light of the following embodiments.

BRIEF DESCRIPTION OF THE FIGURES

FIG. 1—shows the HPLC traces of two hemp extracts with different ratio between CBDA and CBD and related RT.

EXPERIMENTAL PART

Materials and Methods
HPLC
Column=Thermo Accucore C18 (100×4.6 mm; 2.6 µm).
Temperature=50° C.
Eluting phase=in gradient–water (H3PO4 0.05%)/acetonitrile.
Detector=UV (200-210 nm).
RT (CBDA)=about 4 minutes
RT (CBD)=about 5 minutes Example 1: Obtaining CBD from Hemp Having a CBDA/CBD Ratio of about 70/30 by Extraction and Separation of its Acidic Form (CBDA) (Process A) (Tests Q207D/394 and Q207D/396)

Hexane Extraction from Biomass (Test Q207D/394):

132 Kg of hexane and 40 kg of micronized hemp were introduced into a 250-liter steel jacketed reactor equipped with a stirrer shaft while stirring at a temperature of 20° C. for 4 hours.

After this time, the suspension has been discharged from the reactor and filtered under vacuum in 2 aliquots. The biomass retained by the filter in each aliquot has been washed with 10 liters of hexane.

The filtered solution has been reloaded in the reactor and concentrated under vacuum at a temperature <35° C. at the minimum possible volume. 7.48 kg of concentrated solution containing 508.64 g of CBDA+125.7 g of CBD have been obtained (values obtained by HPLC analysis).

The concentrated solution has been kept at a temperature of <30° C. for the subsequent phases.

Separation of the CBDA from the CBD (Test Q207D/396):

1001.0 g (containing 77.7 g of CBDA+16.8 g of CBD) of the concentrated solution, 540 ml of methanol, 810 ml of demineralized water and 5 g sodium bisulfite in a 3-liter four-neck glass flask equipped with a stirrer shaft have been introduced. The pH has been corrected to 12.0 under stirring by adding a 30% NaOH solution (about 125 ml). The whole has been transferred to a separatory funnel for the separation of the upper hexane phase (1) from the lower methanol-aqueous phase (1).

The separatory funnel has been unloaded keeping the two phases separate and transferring the upper hexane phase (1) back into the four-neck flask in which 160 ml of methanol, 240 ml of demineralized water and 5 g sodium bisulfite have been introduced while stirring. The pH has been adjusted to 12.5 by adding of a 30% NaOH solution.

The whole has been transferred into the separatory funnel for the separation of the upper hexane phase (2) from the lower methanol-aqueous phase (2).

The two methanol-aqueous phases (1) and (2) have been pooled into the four-necked flask and 400 ml of hexane have been added thereto. The pH has been lowered under stirring to 5.5 by addition of glacial acetic acid and the whole has been transferred into the separatory funnel to allow the separation of the upper hexane phase (3) from the lower methanol-aqueous phase (3).

The hexane phase (2) has been transferred to the 4-neck flask and an equal volume of demineralized water has been added to it. The pH has been lowered to 5.5 under stirring by adding glacial acetic acid and the whole has been transferred into the separatory funnel for separation of the upper hexane phase (4) from the lower aqueous phase (4).

Results (HPLC Analysis):

| Sample | Weight (grams) | CBDA (grams) | CBD (grams) |
|---|---|---|---|
| Hexane phase (3) | 89.7 | 75.1 | 1.80 |
| Hexane phase (4) | 1156.6 | 4.27 | 18.56 |

Decarboxylation of the CBDA Contained in the Hexane Phase (3):

The hexane phase (3) has been placed in a 500 ml 4-neck flask equipped with stirrer shaft and condenser for the recovery of the distilled hexane and subjected to decarboxylation in a glycerin bath heated at a temperature of 120° C. under stirring for about 7 hours. The solution concentrated to oil has been cooled to R.T., diluted with 150 ml of hexane and filtered on a panel of fossil flour under vacuum.

The filtered solution has been then reconcentrated by means of a rotary evaporator at a temperature of 45° C., obtaining 77.7 g of oil (containing 65.9 g of CBD).

Crystallization of the CBD:

The 77.7 g of oil have been transferred into a 250 ml 4-neck glass flask equipped with a stirrer shaft and 77 ml of hexane have been added thereto. The whole has been stirred for 3 hours in a cold room at 4° C. After this time the crystalline solid was been filtered (always in a cold room at 4° C.) on Gouch (G3) and washed with two 25 ml aliquots each of cold hexane. 46.5 g of crystal with an HPLC purity of 98.9% have been obtained.

Recovery of CBD from the Mother Liquors of Crystallization:

The mother liquors obtained from the previous crystallization step have been concentrated by means of a rotary evaporator at a temperature of 45° C., obtaining 31 g of oil which has been transferred into a 100 ml 4-neck flask (equipped with a stirrer shaft) in a cold room at 4° C. 15 ml of hexane have been added to the oil. The whole has been kept under stirring for 6 hours. After this time the crystalline solid has been filtered (always in a cold room at 4° C.) on Gouch (G3) and washed with three aliquots of 5 ml each of cold hexane. 6.0 g of crystal have been obtained with a 97.9% HPLC purity.

Example 2: Recovery of CBD and CBDA Present in the First Hexane Phase (Process A) by Chromatography (Process B) Test No Q207F/594

Waxes Elimination:

87.7 g of the first hexane phase obtained according to the method (A) containing 1.98 g of CBD and 0.48 g of CBDA have been concentrated to oil by means of a rotary evaporator under vacuum at a temperature of 50° C. 50 ml of methanol have been added to the oil and the whole has been transferred to −20° C. for one night. The suspension has been filtered under vacuum on a Gouch (G3) filtering funnel and the waxes retained by the filter have been washed with two 50 ml aliquots of cold methanol. The filtered product has been concentrated by means of a rotary evaporator under vacuum at a temperature of 50° C., obtaining 8.1 g of oil containing 1.60 g of CBD and 0.31 g of CBDA.

Silica Gel Chromatography:

100 g of silica gel have been packed in a glass column (ø5 cm×h 20 cm) and equilibrated in equicurrent with 250 ml of mobile phase (hexane-ethyl acetate 10:1). 8.1 g of oil from the previous step have been loaded on the column after having diluted them with about 8 ml of mobile phase. The elution took place by fall and 12 fractions of 22 g each have been collected. On fractions from n°4 to n°12 included, an HPLC analysis has been performed to verify the CBD content and the relative purity.

Results:

| Fraction No | Content CBD (g/100 g) | Purity CBD (area %) |
| --- | --- | --- |
| 4 | 0.11 | 77.68 |
| 5 | 1.16 | 92.52 |
| 6 | 1.96 | 91.97 |
| 7 | 1.53 | 88.50 |
| 8 | 1.06 | 81.99 |
| 9 | 0.62 | 73.69 |
| 10 | 0.36 | 63.93 |
| 11 | 0.18 | 54.17 |
| 12 | 0.08 | 37.48 |

A pool of fractions has been obtained from n°4 to n°9 included (high purity fractions) with a total CBD content of 1.41 g and a fraction pool from n°10 to n°12 included (fractions to average purity) with a total CBD content of 0.138 g.

Example 3: Obtaining CBD in a Laboratory Scale from Hemp Having a CBDA/CBD Ratio of about 90/10 by Extraction and Separation of its Acid Form (CBDA) (Process A) (Test Q207E/515)

Hexane Extraction from Biomass:

2 kg of micronized hemp and 10 liters of hexane (mixture of isomers) are introduced into a 15-liter glass flask equipped with a stirrer shaft. The whole has been kept under stirring at room temperature for 4 hours. After this time, the suspension has been filtered on filter paper by Buchner funnel under vacuum by washing the biomass on the filter with 6 liters of hexane. The filtered product has been concentrated by means of a rotary evaporator, under vacuum at a temperature of 30° C. up to a volume of 860 ml.

Separation of the CBDA from the CBD:

The filtered solution containing 21.23 g of CBDA and 1.8 g of CBD (values obtained from the HPLC analysis) has been introduced into a 3-liter 4-neck glass flask equipped with a stirrer shaft and to it have been added 478 ml of methanol and 360 ml of demineralized water.

The pH has been increased to 8.2 by addition, with vigorous stirring, of about 7 ml of a 30% NaOH solution.

The whole has been transferred to a separatory funnel for the separation of the upper hexane phase (1) from the lower methanol-aqueous phase (1).

The methanol-aqueous phase (1) has been transferred back into the 4-neck flask and 740 ml of hexane (mixture of isomers) have been added under stirring. The pH has been adjusted to 5.0 by adding about 20 ml of glacial acetic acid.

The whole has been transferred into a separatory funnel for the separation of the upper hexane phase (2) from the lower methanol-aqueous phase (2).

| Sample | Weight (grams) | CBDA (grams) | CBD (grams) |
| --- | --- | --- | --- |
| Hexane phase (1) | 619.4 | 4.03 | 1.8 |
| Hexane phase (2) | 499.1 | 15.95 | — |

Decarboxylation of the CBDA Contained in the Hexane Phase (2):

The hexane phase (2) has been placed in a 1-liter 4-neck flask equipped with stirrer shaft and condenser for the recovery of the distilled hexane and subjected to decarboxylation in a glycerin bath heated at a temperature of 120° C. under stirring for about 4 hours.

Crystallization of the CBD:

The solution containing the CBD has been concentrated by rotary evaporator under vacuum at a temperature of 50° C., obtaining 24.3 g of oil which has been diluted with 14.5 ml of hexane (mixture of isomers) and placed in a cold room at 4° C. overnight. After this time, the suspension has been filtered on Gouch (G3) and the crystal has been washed with 6 ml of cold hexane. 10.1 g of wet crystal CBD have been obtained with a purity of 99.6% and 42.2 g of mother liquor containing 3.88 g of CBD

Example 4: Obtaining in a Pilot Scale of CBD from Hemp Having a CBDA/CBD Ratio of about 90/10 by Extraction and Separation of its Acidic Form (CBDA) (Process A) (Product P56/38/047)

Hexane Extraction from Biomass:

150 kg of micronized hemp and 700 liters of hexane (mixture of isomers) were introduced in a steel dryer filter equipped with stirring system. The whole was kept under stirring for 1 hour at room temperature. After this time the stirring has been stopped and the suspension has been filtered by nitrogen pressure. The filtered product containing CBDA has been collected in a cistern. The biomass retained by the filter has been washed with two 450-liter aliquots of hexane each while maintaining the whole under stirring at room temperature for one hour and discharging the filtrate each time into the collection cistern by nitrogen pressure.

The exhausted biomass has been discharged from the drying filter in which an additional 150 kg of fresh micronized hemp have been loaded for a second extraction.

Preconcentration:

The filtered solutions obtained from two extractions of 150 Kg of hemp each have been pooled in a jacketed steel reactor equipped with a stirring system and condenser and concentrated under vacuum at a temperature of 30° C. up to a volume of about 180 liters.

Separation of the CBDA from the CBD:

180 liters of preconcentrated solution have been loaded into a 250-liter steel jacketed reactor equipped with a stirrer shaft and a condenser and concentrated under vacuum at a temperature between 16 and 20° C. at a final volume of about 130 liters. 54 liters of drinking water have been loaded into the reactor with 57 liters of methanol. The pH was brought to 8.2, under stirring, by adding a 30% sodium hydroxide solution. Everything has been kept static at rest for 60 minutes. The two phases have been separately discharged and the hydro-alcoholic phase has been recharged in the reactor and 76.6 Kg of hexane (mixture of isomers) were added to it. The pH has been brought under stirring to 5.0 by adding 3.75 liters of glacial acetic acid and the whole has been kept static at rest for one hour.

The lower hydroalcoholic phase (115 Kg) has been discharged into a tank for disposal while the upper hexane phase has been concentrated under vacuum at a temperature of about 50° C. obtaining a final weight of about 27 Kg and recovered for the subsequent decarboxylation phase.

Decarboxylation of the CBDA Contained in the Hexanic Phase (2):

4 hexane phases from the previous steps containing 14.48 Kg of CBDA (from the HPLC analysis) have been pooled in a 250-liter steel jacketed reactor equipped with a stirring shaft and concentrated at a temperature of 50° C. up to oil. The temperature has been brought to about 120° C. while stirring for 4 hours. After this time, 13.6 Kg of hexane (mixture of isomers) have been added into the reactor and 30.3 Kg of solution has been discharged for the subsequent crystallization step.

1$^{st}$ Crystallization of the CBD:

30.3 Kg of CBD solution from the previous step have been filtered on paper under vacuum by a Buchner filtering funnel and loaded into a 25 liters glass reactor equipped with a stirrer shaft. The solution has been concentrated to oil under vacuum at a temperature of 50° C. and, after having cooled it to 35° C., 6 Kg of hexane (n-hexane) have been added. The solution has been cooled to 20° C. and the crystallization has been triggered by adding of 20 g of crystal CBD.

After 30 minutes the temperature has been brought to 4° C. keeping under stirring for 12 hours.

The suspension has been filtered on paper under vacuum by a Buchner filter funnel and the crystal has been washed with 6 liters of cold hexane (n-hexane). 8.16 Kg of wet crystal CBD have been obtained with a LOD of 0.33% and a purity of 98.6% and 12.65 Kg of mother liquors containing 2.96 Kg of CBD.

2$^{nd}$ Crystallization of the CBD:

8.16 Kg of crystal CBD coming from the previous step have been loaded into a 25 liters glass reactor equipped with a stirring shaft and joined to 8.48 Kg of hexane (n-hexane) at 35° C. under stirring until complete solubilization. The temperature was brought to 4° C. by performing a descending ramp and maintained for 12 hours.

The suspension has been filtered on paper under vacuum by a Buchner filter funnel and the crystal has been washed with 6.7 liters of cold hexane (n-hexane). 6.94 Kg of wet crystal with a purity of 99.4% and 11.9 Kg of mother liquor containing 625 g of CBD have been obtained.

Example 5: Obtaining CBD by Silica Gel Chromatography on Industrial Scale (Process B)

Methanolic Extraction of CBD from Biomass (See FDL #2728PF_01_01):

In a 6000-liter steel reactor, jacketed equipped with a stirrer shaft, have been introduced 3500 kg of methanol and, under stirring, 1000 kg of micronized biomass. The temperature has been brought to 63-67° C. at reflux. The whole has been kept under stirring until the percentage of CBDA was 7% with respect to the CBD (about 60 hours). After decreasing the internal temperature of the reactor at 15-25° C., the suspension has been filtered by centrifugation on canvas at 450-500 rpm for 20-25 minutes washing the biomass 3 times with about 20 kg of methanol for 25-30 minutes. For the wax component elimination, the filtered solution has been recharged in the reactor and concentrated under vacuum at a temperature of 50° C., until obtaining an agitable oily residue to which 300 liters of methanol have been added. The reactor temperature has been brought to 63-67° C. by distilling under vacuum at reflux for 30 minutes. After this time, the temperature has been lowered to −5--10° C. and the suspension has been kept in slow stirring for about 12 hours at the end of which the temperature has been increased to 5-10° C. 22 Kg of fossil flour have been added under stirring and the suspension has been filtered by centrifugation on canvas at 450-500 rpm for 60 minutes performing 3 washes with about 40 kg of cold methanol (5-10° C.) each for 35-40 minutes.

Elimination of Pitches (See FDL #2728PF_02_01):

The filtered solution has been charged back into the reactor and concentrated under vacuum at a temperature of 50° C. until obtaining a stirrable oily residue, to which 400 liters of methanol have been added. The reactor temperature has been brought to 63-67° C. by distilling under vacuum at reflux for 30 minutes. After this time the temperature has been lowered to 15-25° C. and 150 Kg of hexane and 150 liters of demineralized water have been loaded into the reactor. The mixture has been kept under stirring at a temperature of 15-25° C. for 30 minutes and static for additional 30 minutes to allow the separation of the lower methanol-aqueous phase (1) from the upper hexane phase (1). The methanol-aqueous phase (1) has been transferred to a second reactor in which 75 kg of hexane have been also introduced. The mixture has been kept under stirring at a temperature of 15-25° C. for 30 minutes and static for additional 30 minutes to allow the separation of the lower methanol-aqueous phase (2) from the upper hexane phase (2). The methanol-aqueous phase (2) has been discharged from the reactor in which the hexane phase (1) has been introduced. The two hexane phases thus pooled have been concentrated under vacuum at a temperature of 50° C. obtaining 43 kg of concentrated solution. A sample of concentrated product has been taken for the determination of the CBD content.

Results:
Dry weight=43.9 Kg
Total content of CBD=16.0 Kg
CBD/dry weight ratio×100=36.4%
Silica Gel Chromatography (See FLD #2728PF_03A_01):
A steel column (ø80 cm×h 200 cm) has been packed with 400 kg of silica gel and balanced in equicurrent with 1000 liters of mobile phase (hexane-ethyl acetate 10:1) at a flow of 250-300 liters/hour.
43.9 Kg of extract pitches-free have been diluted with hexane (mixture of isomers) up to a total weight of 54 kg and loaded onto the column. The elution occurred in equicurrent with the mobile phase (hexane-ethyl acetate 10:1) at a flow of 250-300 liters/hour. 11 fractions of 100 Kg each have been collected on which an HPLC analysis has been performed to verify the CBD content and the relative purity.
Results

| Fraction No | CBD Content (g/100 g) | CBD Purity (area %) |
|---|---|---|
| 1 | 0.003 | 9.5 |
| 2 | 0.059 | 26.3 |
| 3 | 2.800 | 91.7 |
| 4 | 4.077 | 91.0 |
| 5 | 2.803 | 88.3 |
| 6 | 1.974 | 86.6 |
| 7 | 1.213 | 84.7 |
| 8 | 0.866 | 83.9 |
| 9 | 0.482 | 81.1 |
| 10 | 0.246 | 75.7 |
| 11 | 0.169 | 70.7 |

Fractions having an HPLC purity ranging from 86.6% to 91.7% (high purity fraction pool) have been pooled for the subsequent crystallization step. Fractions having a purity from 81.1% to 84.7% have been pooled (fractional pools of medium purity) and purified again on the column after having been combined with other fractions of medium purities from other chromatographies.
$1^{st}$ Crystallization of the CBD (See FDL #2728PF_01_02):
69.5 Kg of pool of high purity fractions coming from two different purifications on silica gel and containing 25.27 Kg of CBD have been collected, vacuum-filtered on canvas, loaded in a 250-liters steel jacketed reactor and equipped of stirrer shaft and concentrated to oil under vacuum at a temperature of 45° C. At the end of the concentration, the temperature was raised to 70° C. maintaining stirring for 3 hours. After this time, the temperature has been lowered to 30° C. and 18 liters of hexane (mixture of isomers) have been added. The temperature has been lowered to 15-21° C. and the crystallization has been triggered by adding 20 g of CBD crystal. The temperature has been lowered further to 4° C. and the whole has been kept under stirring for 12 hours. The suspension has been discharged from the reactor and the "raw" CBD crystal has been recovered by vacuum filtration on canvas by performing three washings of the crystals with a total of 12.6 liters of cold hexane. 20 Kg of wet crystal CBD have been obtained (with an HPLC purity of 99.22%) with a LOD of 7.9% equivalent to 18.4 Kg of dried product and 32 Kg of crystallization mother liquor.
Recovery of CBD from Crystallization Mother Liquors (See FDL #2728PF_01_02):
23 Kg of crystallization mother liquids have been concentrated in a glass jacketed 25-liter reactor equipped with a vacuum stirrer shaft at a temperature of 50° C. up to a volume of 19 liters. 5 liters of hexane (mixture of isomers) have been added and, after having brought the temperature to 4° C., the crystallization has been triggered by the addition of 7 g of crystal CBD, maintaining at 4° C. under stirring overnight. The suspension has been filtered under vacuum on paper and the crystal has been washed with 2 liters of cold hexane (mixture of isomers).
3.2 kg of wet crystal have been obtained (with an HPLC purity of 95.94%).

Example 6: Crystallization of CBD in Methylcyclohexane (Test Q207F/576B)

25 g of CBD crystal obtained by the Process A according to example 4 have been dissolved at room temperature under stirring with 250 ml of hexane (mixture of isomers) in a 500 ml glass flask equipped with magnetic stirrer bar and left static overnight. The solution has been filtered twice under vacuum on a glass fiber filter with a porosity of 0.8 μm and concentrated to oil by a rotary evaporator at a temperature of 50° C.
50 ml of methylcyclohexane have been added to the oil and the whole has been placed at a temperature of 4° C. under stirring for one night.
The suspension has been filtered under vacuum on a Gouch (G3) filter funnel and the crystal has been washed with 20 ml of cold methylcyclohexane.
16.9 g of wet crystal have been obtained with an HPLC purity of 99.05% and 24 g of mother liquor.

Example 7: Crystallization of CBD in Heptane (Test Q207F/584)

22.1 g of crystal CBD obtained by the Process A according to example 4 have been dissolved under stirring at a temperature of 38° C. with 45 ml of heptane in a 100 ml glass flask equipped with a magnetic stirrer bar. The solution has been brought to 4° C. and the crystallization has been triggered by adding a crystal CBD spatula tip while keeping the whole stirred by magnetic stirrer bar for one night.
The suspension has been filtered under vacuum on a Gouch (G3) filter funnel and the crystal has been washed with two 10 ml aliquots of cold heptane.
20.1 g of wet crystal have been obtained with an HPLC purity of 99.2% and 36.4 g of mother liquor.

The invention claimed is:
1. A process for the production of cannabidiol (CBD) or another neutral cannabinoid, said process comprising:
i) contacting a biomass containing
cannabidiolic acid (CBDA),
CBD and CBDA,
another cannabinoid carboxylic acid, or
said another cannabinoid carboxylic acid and a neutral cannabinoid, with an extraction solvent for at least 10 minutes at a temperature between 0° C. and the reflux temperature of the solvent, to obtain, after biomass removal, an extraction solution; said extraction solvent selected from the group consisting of pentane, hexane, heptane, octane, methylcyclohexane, ethyl acetate, toluene, methylene chloride, and mixtures thereof;
ii-a) contacting the extraction solution with hydro-alcoholic solution consisting of water and
an alcohol selected from the group consisting of propanol, ethanol, methanol, and mixtures thereof,
and adjusting pH to 7.5-12.5 by adding a suitable alkaline solution, to obtain, after phases separation, a first hydro-alcoholic phase and a first organic phase;

iii-a) contacting the first hydro-alcoholic phase with a second water-immiscible solvent and an acid solution adapted to bring pH to 2.0-6.5 to obtain a second organic phase and a second hydro-alcoholic phase; said second water-immiscible solvent selected from the group consisting of pentane, hexane, heptane, methylcyclohexane, and mixtures thereof;

iv-a) concentrating the second organic phase and subjecting the resulting oil to heating at a temperature between 65° C. and 180° C. for a time period of at least 10 minutes to obtain the decarboxylation of CBDA to CBD; and v) crystallizing CBD, or said another neutral cannabinoid, from a third water-immiscible solvent selected from the group consisting of pentane, hexane, heptane, octane, methylcyclohexane, and mixtures thereof.

2. A process for the production of cannabidiol (CBD) or another neutral cannabinoid, said process comprising:

i) contacting a biomass containing
CBD,
CBD and CBDA,
said another neutral cannabinoid, or
said another neutral cannabinoid and a cannabidiolic acid in the form of carboxylic acid, with an extraction solvent for at least 10 minutes at the reflux temperature of the solvent, to obtain, after biomass removal, an extraction solution; said extraction solvent selected from the group consisting of hexane, heptane, acetone, propanol, ethanol, methanol, ethyl acetate, toluene, methylene chloride, and mixtures thereof;

ii-b) removing waxes by concentrating the extraction solution up to obtain an extraction oil and contacting the extraction oil with an alcohol at a temperature of 4-10° C. for at least 10 minutes to obtain a suspension of extract and waxes, said alcohol selected from the group consisting of methanol, ethanol, propanol, and mixtures thereof; filtering and concentrating the suspension to obtain a wax-free extraction oil;

iii-b) removing pitches by contacting the wax-free extraction oil with an organic water-immiscible solvent and a hydro-alcoholic solution to obtain an organic phase containing the wax- and pitch-free extract and a pitch-containing hydro-alcoholic phase;

iv-b) subjecting the wax- and pitch-free oil to single silica gel chromatography using a suitable eluent phase and collecting the fractions containing CBD, or said another neutral cannabinoid; and v) crystallizing CBD, or said another neutral cannabinoid, from a third water-immiscible solvent selected from the group consisting of pentane, hexane, heptane, octane, methylcyclohexane, and mixtures thereof.

3. The process according to claim 1, wherein the biomass is selected from the group consisting of *Cannabis sativa*, Antal, Armanca, Beniko, Bialobrzeskie, Cannakomp, Carma, Carmagnola, Carmaleonte, Chamaeleon, Codimoro, CS, Dacia Sacuieni, Delta-Ilosa, Delta-405, Denise, Diana, Dioica 88, Eletta Campana, Epsilon 68, Fedora 17, Felina 32, Férimon, Fibranova, Fibrol, Finola, Futura 75, Ivory, KC Bonusz, KC Dora, KC Virtus, KC Zuzuna, Kompolti, KompoltiHibrid TC, Lipko, Lovrin 110, Marcello, Markant, Monica, Raj an, Ratza, Santhica 23, Santhica 27, Santhica 70, SecuieniJubileu, Silvana, Szarvasi, Tiborszallasi, Tisza, Tygra, Uniko B, Uso-31, Wielkopolkie, Wojko, and Zenit.

4. The process according to claim 2, wherein the biomass is selected from the group consisting of *Cannabis sativa*, Antal, Armanca, Beniko, Bialobrzeskie, Cannakomp, Carma, Carmagnola, Carmaleonte, Chamaeleon, Codimoro, CS, Dacia Sacuieni, Delta-Ilosa, Delta-405, Denise, Diana, Dioica 88, Eletta Campana, Epsilon 68, Fedora 17, Felina 32, Férimon, Fibranova, Fibrol, Finola, Futura 75, Ivory, KC Bonusz, KC Dora, KC Virtus, KC Zuzuna, Kompolti, KompoltiHibrid TC, Lipko, Lovrin 110, Marcello, Markant, Monica, Raj an, Ratza, Santhica 23, Santhica 27, Santhica 70, SecuieniJubileu, Silvana, Szarvasi, Tiborszallasi, Tisza, Tygra, Uniko B, Uso-31, Wielkopolkie, Wojko, and Zenit.

5. The process according to claim 1, wherein the biomass is micronized before being subjected to solvent extraction.

6. The process according to claim 2, wherein the biomass is micronized before being subjected to solvent extraction.

7. The process according to claim 1, wherein the extraction at step (i) is carried out at a temperature between 0° C. and 35° C. for a time period of at least 10 minutes while keeping the cannabis in contact with an extraction solvent selected from the group consisting of pentane, hexane, heptane, octane, methylcyclohexane, and mixtures thereof.

8. The process according to claim 7, wherein the extraction solvent is hexane and the extraction is carried out at a temperature between 10° C. and 25° C.

9. The process according to claim 1, wherein in step (ii-a) the alcohol is selected from the group consisting of ethanol and methanol, and the pH is adjusted to between 8.0 and 8.5 by adding a suitable alkaline solution.

10. The process according to claim 9, wherein the hydro-alcoholic solution of step (ii-a) is methanol.

11. The process according to claim 1, wherein the pH of step (iii-a) is adjusted to between 4.5 and 5.5 by adding an acetic acid solution.

12. A The process according to claim 1 further comprising:

ii-b) removing waxes by concentrating the first organic phase up to obtain an extraction oil and contacting the extraction oil with an alcohol at a temperature of 4-10° C. for at least 10 minutes to obtain a suspension of extract and waxes, said alcohol selected from the group consisting of methanol, ethanol, propanol, and mixtures thereof; filtering and concentrating the suspension to obtain a wax-free extraction oil;

iii-b) removing pitches by contacting the wax-free extraction oil with an organic water-immiscible solvent and a hydro-alcoholic solution to obtain a third organic phase containing the wax- and pitch-free extract and a hydro-alcoholic pitch-containing phase; concentrating the third organic phase containing the wax- and pitch-free extract to obtain a wax- and pitch-free oil;

iv-b) subjecting the wax- and pitch-free oil to single silica gel chromatography using a suitable eluent phase and collecting the fractions containing CBD, or said another neutral cannabinoid; and v) crystallizing CBD, or said another neutral cannabinoid, from the third water-immiscible solvent.

13. The process according to claim 2, wherein the extraction at step (i) is carried out while keeping the cannabis in contact with an extraction solvent selected from the group consisting of acetone, propanol, ethanol, methanol, ethyl acetate, toluene, n-hexane, or hexane-mixture of isomers.

14. The process according to claim 2, wherein in step (ii-b) the alcohol is methanol.

15. The process according to claim 14, wherein the temperature is 4° C.

16. The process according to claim 2, wherein in step (iii-b) the pitches are removed from the wax-free extraction oil by adding, under stirring, a solvent selected from the group consisting of toluene, pentane, hexane, heptane, octane, and mixtures thereof, and a hydro-alcoholic solution wherein the alcohol is selected from the group consisting of ethanol and methanol.

17. The process according to claim 16, wherein the solvent is hexane and the alcohol of the hydro-alcoholic solution is methanol.

18. The process according to claim 2, wherein in step (iv-b) the eluent phase is a hexane and ethyl acetate mixture.

19. The process according to claim 18, wherein the hexane and ethyl acetate mixture is in a ratio between 20:1 and 5:1.

20. The process according to claim 18, wherein the hexane is n-hexane or a hexane isomer mixture.

21. The process according to claim 2, wherein the biomass is contacted with the extraction solvent at reflux temperature of the solvent until almost all CBDA has been decarboxylated to CBD.

22. The process according to claim 12, wherein in step (ii-b) the alcohol is methanol.

23. The process according to claim 21, wherein the temperature is 4° C.

24. The process according to claim 12, wherein in step (iii-b) the pitches are removed from the wax-free extraction oil by adding, under stirring, a solvent selected from the group consisting of toluene, pentane, hexane, heptane, octane, and mixtures thereof, and a hydro-alcoholic solution wherein the alcohol is selected from the group consisting of ethanol and methanol.

25. The process according to claim 24, wherein the solvent is hexane and the alcohol of the hydro-alcoholic solution is methanol.

26. The process according to claim 12, wherein in step (iv-b) the eluent phase is a hexane and ethyl acetate mixture.

27. The process according to claim 26, wherein the hexane and ethyl acetate mixture is in a ratio between 20:1 and 5:1.

28. The process according to claim 25, wherein the hexane is n-hexane or a hexane isomer mixture.

29. A process for the production of cannabidiol (CBD) or another neutral cannabinoid, said process comprising:
   i) contacting a biomass containing cannabidiolic acid (CBDA) or CBDA and CBD, or said another cannabinoid carboxylic acid or said another cannabinoid carboxylic acid and neutral cannabinoid, with an extraction solvent for at least 10 minutes at a temperature between 0° C. and the reflux temperature of the solvent, to obtain, after biomass removal, an extraction solution; said extraction solvent selected from the group consisting of propanol, ethanol, methanol, and mixtures thereof;
   ii-a) contacting the extraction solution with a hydro-alcoholic solution and adjusting pH to 7.5-12.5 with a suitable alkaline solution adding also a first water-immiscible solvent selected from the group consisting of pentane, hexane, heptane, methylcyclohexane, and mixtures thereof; to obtain, after phase separation, a first hydro-alcoholic phase and a first organic phase;
   iii-a) contacting the first hydro-alcoholic phase with a second water-immiscible solvent and an acid solution adapted to bring pH to 2.0-6.5 to obtain a second organic phase and a second hydro-alcoholic phase; said second water-immiscible solvent selected from the group consisting of pentane, hexane, heptane, methylcyclohexane, and mixtures thereof;
   iv-a) concentrating the second organic phase and subjecting the resulting oil to heating at a temperature between 65° C. and 180° C. for a time period of at least 10 minutes to obtain the decarboxylation of CBDA to CBD; and
   v) crystallizing CBD, or said another neutral cannabinoid, from a third water-immiscible solvent selected from the group consisting of pentane, hexane, heptane, octane, methylcyclohexane, and mixtures thereof.

30. The process according to claim 29, wherein the biomass is selected from the group consisting of *Cannabis sativa*, Antal, Armanca, Beniko, Bialobrzeskie, Cannakomp, Carma, Carmagnola, Carmaleonte, Chamaeleon, Codimoro, CS, Dacia Sacuieni, Delta-Ilosa, Delta-405, Denise, Diana, Dioica 88, Eletta Campana, Epsilon 68, Fedora 17, Felina 32, Férimon, Fibranova, Fibrol, Finola, Futura 75, Ivory, KC Bonusz, KC Dora, KC Virtus, KC Zuzuna, Kompolti, KompoltiHibrid TC, Lipko, Lovrin 110, Marcello, Markant, Monica, Raj an, Ratza, Santhica 23, Santhica 27, Santhica 70, SecuieniJubileu, Silvana, Szarvasi, Tiborszallasi, Tisza, Tygra, Uniko B, Uso-31, Wielkopolkie, Wojko, and Zenit.

31. The process according to claim 29, wherein the biomass is micronized before being subjected to solvent extraction.

32. The process according to claim 29, wherein the extraction solvent in step (i) is methanol.

33. The process according to claim 29, wherein in step (ii-a) the pH is adjusted to between 8.0 and 8.5 by adding a suitable alkaline solution.

34. The process according to claim 1, wherein the pH of step (iii-a) is adjusted to between 4.5 and 5.5 by adding an acetic acid solution.

\* \* \* \* \*